(12) United States Patent
Boebel et al.

(10) Patent No.: US 7,025,720 B2
(45) Date of Patent: Apr. 11, 2006

(54) HYSTEROSCOPE WITH A SHANK EXCHANGE SYSTEM

(75) Inventors: Manfred Boebel, Bauschlott (DE); Sybille Bruestle, Sternenfels (DE)

(73) Assignee: Richard Wolf GmbH, Knittlingen (DE)

( * ) Notice: Subject to any disclaimer, the term of this patent is extended or adjusted under 35 U.S.C. 154(b) by 58 days.

(21) Appl. No.: 10/330,885

(22) Filed: Dec. 27, 2002

(65) Prior Publication Data
US 2003/0125607 A1   Jul. 3, 2003

(30) Foreign Application Priority Data
Dec. 28, 2001 (DE) ................................ 101 64 384

(51) Int. Cl.
*A61B 1/00* (2006.01)
(52) U.S. Cl. .................... 600/105; 600/135
(58) Field of Classification Search ............ 600/135, 600/136, 138, 105, 200, 121, 123, 133, 153, 600/160
See application file for complete search history.

(56) References Cited

U.S. PATENT DOCUMENTS

| | | | | |
|---|---|---|---|---|
| 4,567,880 A | * | 2/1986 | Goodman ................... | 600/135 |
| 4,911,148 A | * | 3/1990 | Sosnowski et al. ......... | 600/136 |
| 5,257,617 A | * | 11/1993 | Takahashi ................... | 600/123 |
| 5,320,091 A | * | 6/1994 | Grossi et al. ............... | 600/104 |
| 5,545,121 A | * | 8/1996 | Yabe et al. ................. | 600/121 |
| 5,582,575 A | | 12/1996 | Heckele et al. | |
| 5,725,475 A | * | 3/1998 | Yasui et al. ................. | 600/127 |
| 6,358,200 B1 | * | 3/2002 | Grossi ........................ | 600/156 |
| 6,361,489 B1 | * | 3/2002 | Tsai ........................... | 600/109 |
| 6,383,133 B1 | * | 5/2002 | Jones ......................... | 600/200 |
| 6,554,765 B1 | * | 4/2003 | Yarush et al. .............. | 600/132 |
| 6,645,140 B1 | * | 11/2003 | Brommersma ............. | 600/128 |

FOREIGN PATENT DOCUMENTS

| | | |
|---|---|---|
| DE | 33 19 049 A1 | 5/1984 |
| DE | 33 41 385 A1 | 5/1984 |
| DE | 36 44728 C1 | 11/1987 |
| DE | 44 45 105 A1 | 5/1996 |
| DE | 297 20 643 U1 | 2/1998 |
| DE | 196 31 677 C1 | 4/1998 |
| DE | 197 51 632 C1 | 9/1999 |
| DE | 100 09 020 A1 | 9/2001 |
| DE | 100 09 020 C2 | 3/2002 |

* cited by examiner

*Primary Examiner*—Beverly M. Flanagan
(74) *Attorney, Agent, or Firm*—Akin Gump Strauss Hauer & Feld, LLP

(57) ABSTRACT

An endoscope has an optics housing provided at a proximal end, with an outer shank releasably connected to the optics housing, and with an inner shank which is arranged inside and parallel to the outer shank and is releasably connected to the optics housing. A corresponding endoscope set and a set of endoscope shanks are also provided.

24 Claims, 4 Drawing Sheets

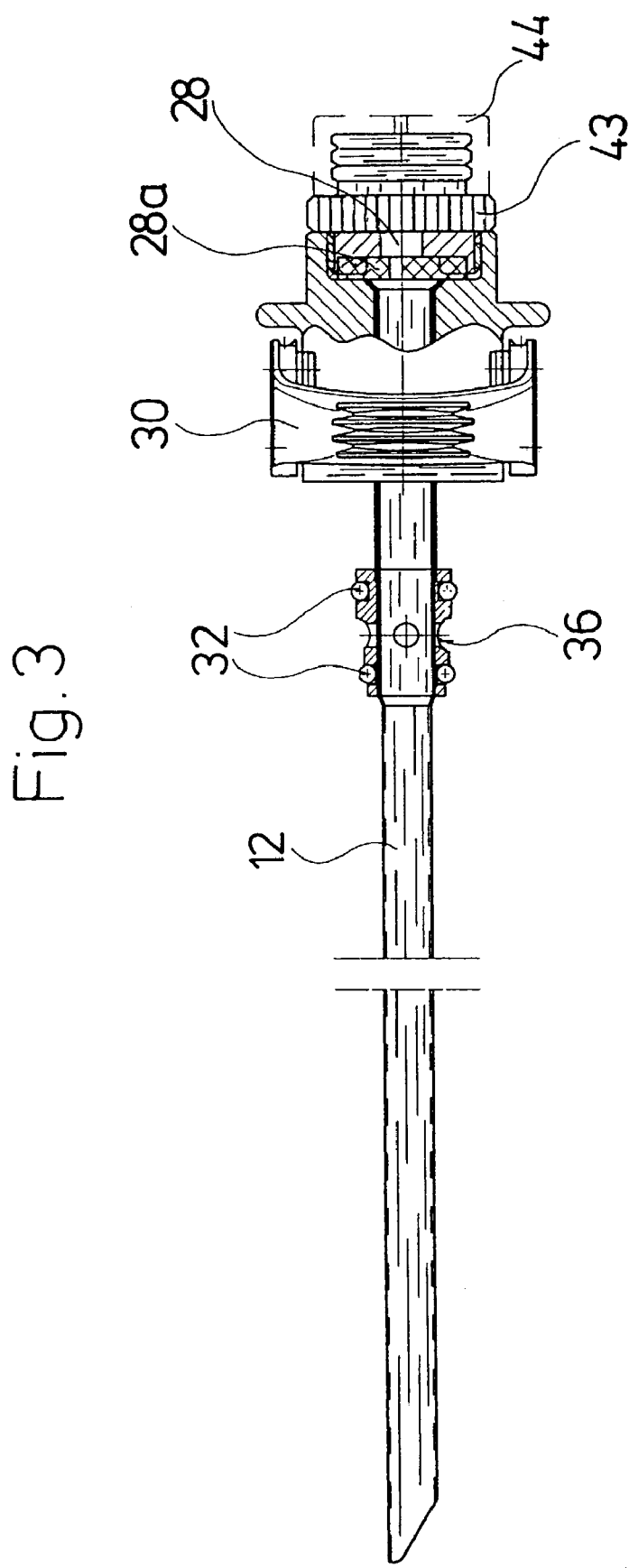

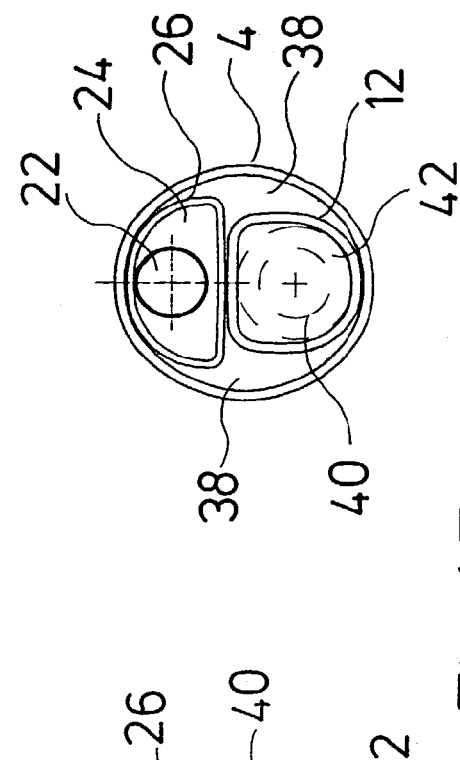
Fig.4A
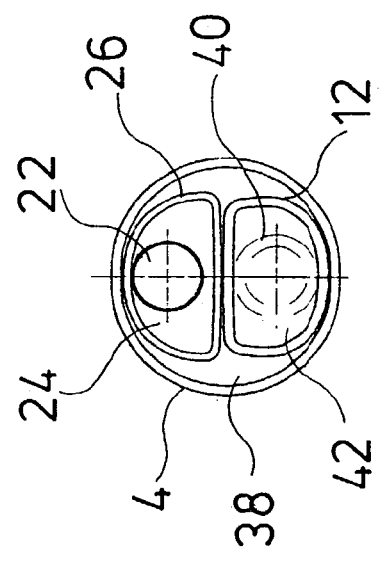
Fig.4B
Fig.4C
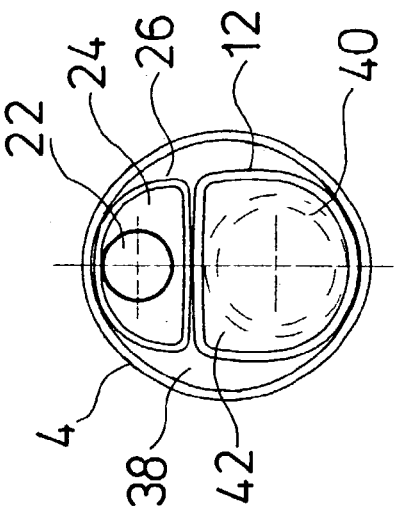
Fig.4D
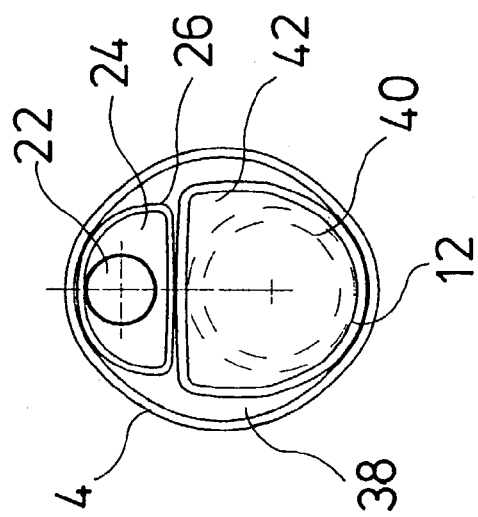
Fig.4E

HYSTEROSCOPE WITH A SHANK EXCHANGE SYSTEM

BACKGROUND OF THE INVENTION

The invention relates to an endoscope, an endoscope set, and a set of shanks for an endoscope.

With endoscopes, for examples hysteroscopes, it is desirable to design the endoscope shank with as small an outer diameter as possible. The minimum outer diameter is, however, in particular set by the size of the instruments to be introduced. With known endoscopes, for example hysteroscopes, the operator usually begins with an instrument and an endoscope which has the smallest possible diameter. When required, this instrument is exchanged by an instrument which has a larger diameter. This may be the case if larger quantities of tissue are to be removed from the body cavity. In this case then, an endoscope with a larger instrument channel diameter is required. Since the channels arranged in the inside of the known endoscopes are matched to one another in a manner such that free space in the endoscope shank is optimally exploited, one must have several endoscopes with different dimensions ready. The provision of several endoscopes of differing sizes entails high costs.

BRIEF SUMMARY OF THE INVENTION

It is the object of the invention to provide an endoscope or an endoscope set with which one avoids having to make available several endoscopes with differing diameters for an operation.

This object is achieved by an endoscope having an optics housing provided at a proximal end, an outer shank releasably connected to the optics housing, and an inner shank running inside and parallel to the outer shank and being releasably connected to the optics housing, the inner and outer shanks running in a longitudinal direction of the endoscope. The object is further achieved by an endoscope set including an optics housing, at least one outer shank releasably connectable to the optics housing, and at least one inner shank arrangeable inside the outer shank and releasably connectable to the optics housing. The object is still further achieved by a set of shanks for an endoscope, the set comprising a plurality of shanks having different cross sectional sizes, wherein all of the shanks have respectively at one end an identically designed receiver for connection to an endoscope optics housing.

The endoscope according to the invention, among other things, comprises working optics which at their proximal end comprise an optics housing with a view arranged preferably laterally at an angle to the longitudinal axis of the instrument. The end of the endoscope or the working optics on the proximal end is the end which is proximal to the operator, while the distal end of the endoscope is introduced into a body opening. An outer shank is releasably connected to the optics housing. The outer shank is the endoscope shank which defines the maximum outer diameter of the instrument part to be introduced into a body opening. Furthermore, there is provided an inner shank which in the inside of the outer shank runs parallel therein and which is likewise releasably connected to the optics housing. The endoscope constructed according to the invention may be, for example, a hysteroscope. The outer shank and the inner shank may be removed from the optics housing. The inner shank extends preferably in the longitudinal direction of the instrument through the optics housing. For separation from the optics housing the inner shank is preferably pulled out of the rear of the housing.

According to the invention it is possible to combine different outer and inner shanks with one and the same optics housing. Thus, for an operation with which shanks with different diameters are required, it is no longer necessary to make available several complete endoscopes. Only the endoscope shanks need to be changed. In this manner, the procurement costs may be considerably reduced. Furthermore, the ability to be disassembled favors cleaning and disinfection. The inner shank of the endoscope forms an instrument channel through which various types of instruments may be introduced into the body for carrying out an operation and/or a diagnosis. Instrument shanks with different diameters may be combined with the optics housing, depending on the size of the instrument to be applied. Depending on the outer diameter of the used inner shank, one must select an outer shank with a suitable diameter and this must be exchangeably connected to the optics housing.

The inner shank is usefully designed to be removable from the outer shank. This arrangement permits the outer and inner shanks to be exchanged independently of one another. The outer and inner shanks thus do not form a unit, but may be separated from one another. It is thus possible to use one and the same outer shank with different inner shanks and one and the same inner shank with different outer shanks. The endoscope constructed in such a manner thus offers a multitude of combination possibilities of different shanks, which permits a comprehensive adaptability of the endoscope to different application purposes. In order to simplify the allocation between the outer shank and a fitting or associated inner shank, the shanks which are preferably matched to one another in pairs may, for example, be distinguished by color or in another suitable manner. Although the use or the exchange of the shanks used with the working optics is effected generally in pairs, there is basically the possibility of using an outer shank with inner shanks which have a smaller diameter. A simultaneous exchange of the outer shank is omitted if, for carrying out a subsequent operation step, one must again fall back on an inner shank with a larger diameter.

Usefully, an optics shank is arranged in the inside of the outer shank and extends in the longitudinal direction of the outer shank. The optics shank contains the optical system of the endoscope and is preferably rigidly connected to the optics housing. Thus, on exchange of the exchangeable outer and inner shanks, the optics shank always remains the same, so that this does not need to be changed depending on the applied outer and inner shanks. The endoscope according to the invention thus allows a single working optics to be used with a plurality of differently dimensioned outer and inner shanks. This reduces the costs of procurement considerably, since it is no longer necessary to keep in store a plurality of complete endoscopes, each with their own working optics. When matching the diameters of the outer and inner shanks, it is to be assumed that the dimensions of the endoscope optics are fixed, i.e., above all, cross sectional geometry and length of the optics.

Preferably, a fiber-optic for illumination is arranged in the optics shank. This is formed by fiber-optic fibers or glass fibers in a known manner.

Furthermore, image transmission optics may be arranged in the optics shank. These may likewise consist of a fiber optic or fiber-optic fibers, which transmit(s) an image through the optics shank to the optics of the optics housing. Alternatively, in place of an optical image recording and image transmission, an electronic image recording and transmission may be effected using a CCD element or the like.

In an alternative embodiment, the optics shank may also be releasably connected to the optics housing. This favors the cleaning and disinfection of the endoscope. Furthermore, it is also possible to use different optics with one and the same optics housing.

Between the inner shank and the inner wall of the outer shank there is preferably formed a free space. Such a free space may, for example, be used as a rinsing channel. For this, it is preferably connected to suitable tubings in the optics housing. Such a free space may, for example, be created in that in an outer shank with an essentially circular cross section one applies an inner shank, likewise with a circular cross section, which has a smaller diameter. The inner shank, which may be connected to the optics apart from accommodating auxiliary instruments, preferably likewise serves as a rinsing channel for supplying a rinsing fluid. For this purpose, the optics housing on the proximal side comprises a preferably blockable tubing connection piece or instrument cock. Also, after introducing an auxiliary instrument, the free space remaining in the inner shank is sufficient to be able to supply the required quantity of rinsing fluid to be introduced into the body cavity.

A free space may also remain between the distally extending optics shank and the inner wall of the outer shank. Even if an optics shank is arranged in the outer shank, the total free space which remains between the outer walls of the inner shank and the optics shank, on the one hand, and the inner wall of the outer shank, on the other hand, may be used for rinsing purposes, in particular for leading away the rinsing fluid. In this manner, without having to provide additional rinsing channels, the cross sectional sizes of the shanks may be optimally exploited so that an endoscope shank may be made available with a minimal diameter.

Preferably, the outer shank and the inner shank are releasably connected to the optics housing via coupling cone connections. Such coupling cone connection are known in the art and permit an easy and rigid fixation of the shanks on the optics housing. Furthermore, they permit a good sealing of the channels formed by the shanks.

Furthermore, the invention relates to an endoscope set, which comprises an optics housing and at least one outer shank and at least one inner shank. The outer shank is releasably connected to the optics housing so that it may be exchanged. The inner shank may be arranged in the inside of the outer shank, which is designed essentially tubular, and likewise is releasably connectable to the optics housing. The inner shank is likewise designed essentially tubular and forms an instrument channel through which instruments may be introduced into the inside of the body for carrying out an operation or a diagnosis. The releasable arrangement of the outer shank and inner shank permits these shanks to be easily exchanged. Thus, one creates an endoscope which allows differently shaped, i.e., in particular differently dimensioned outer and inner shanks to be used with one an the same optics housing. For example, the outer and inner shanks of differing diameter and differing geometry may be used in order to adapt the endoscope to different application purposes. Furthermore, the releasability of the inner and outer shanks from the optics housing favors the cleaning and disinfection of the endoscope. Preferably, the endoscope set is a hysteroscope set.

The inner shank is preferably arrangeable in the inside of the outer shank in a manner such that it runs eccentrically to the outer shank. In this manner one creates a lumen which is as free as possible inside the outer shank.

Preferably, the endoscope set comprises several exchangeable inner shanks. The inner shanks may be dimensioned differently and be adapted to various application purposes. For use of the endoscope, the desired inner shank is connected to the optics housing.

The several inner shanks preferably have differing cross sectional sizes. In this manner instrument channels with a differently sized cross sectional area may be made available. For example, it is possible to begin an examination or operation with an instrument channel with a small cross sectional size. If then during the treatment one requires a larger instrument channel, the optics housing may be equipped with an inner shank with a larger cross sectional size or diameter.

Preferably, several exchangeable outer shanks are likewise provided in the endoscope set. The outer shanks are adapted to various application purposes and, according to the envisaged application, may be easily fastened on the optics housing and again released.

Preferably, the outer shanks have different cross sectional sizes. Thus, the endoscope may be adapted very easily to different inner channels or inner shanks without have to keep ready a complete set of endoscopes with different endoscope shank diameters. The outer shanks and inner shanks are preferably matched to one another in pairs, so that a suitably dimensioned outer shank is allocated to each inner shank. The simple coupling ability and separating ability to and from the working optics or the optics housing permits the various large shanks to be easily exchanged for one another during a treatment. The construction of the endoscope set thus permits a very comprehensive application and adaptability to various application purposes, without having to keep several different endoscopes ready.

In the endoscope set there is furthermore usefully provided an optics shank which may be arranged in the inside of the outer shank. The optics shank is part of the working optics, extends distally from the optics housing, and is preferably arrangeable eccentrically in the inside of the outer shank. The working optics may contain image transmission optics as well as an illumination source, in a known manner. The illumination source as well as the image transmission optics may consist of fiber-optics, for example glass fibers which conduct light for illumination from the optics housing, and in particular from a fiber-optic cable connection piece present at the optics housing, to the distal end of the endoscope shank and transmit a recorded image from the distal end to the optics housing. Here, preferably, laterally at an angle to the longitudinal axis there is arranged an eyepiece with which the image may be observed. Alternatively, in place of an optic image transmission one may provide an electronic image transmission using a CCD element or the like arranged in the distal shank end. In place of the fiber-optic one may also arrange illumination elements directly at the distal end in the optics shank. Preferably, the image transmission optics or the image bundle is arranged centrally in the optics shank and is surrounded by the fiber-optics for illumination.

The optics shank is preferably rigidly connected to the optics housing. Since with a change in use of the inner and outer shanks with different cross section sizes it is not necessary likewise to use different working optics, an exchange of the optics in most cases may be dispensed with. On exchange of the outer shank, this is pushed over the optics shank and then connected to the optics housing. The size of the used optics shank at the same time represents a limitation for the minimum diameter of the outer shank.

Alternatively, however, the optics shank may also be releasably connectable to the optics housing. Thus, the working optics may also be adapted to various application purposes. Furthermore, the cleaning and disinfection ability of the endoscope is improved.

The envisaged optics shank usefully has a cross sectional size which is smaller than the inner cross sectional size of each outer shank. This allows all outer shanks of the endoscope set to be useable with one and the same optics shank or the same working optics.

Furthermore, according to the invention, there is provided a set of shanks for an endoscope. This set of shanks for an endoscope consists of a plurality of shanks with different cross sectional sizes, wherein all shanks at one end have an identically formed receiver for connection to the working optics or the optics housing. Disregarding the identically formed receiver, the shanks may be adapted to different application purposes, in particular they may have different inner and/or outer cross sectional sizes. It is thus possible to make available a set of endoscope shanks with different diameters or cross sectional sizes, which may be connected to working optics or an optics housing according to the purpose of application. At the same time, each of the shanks of the set may be used with the same working optics or the same optics housing, on account of the identical or standardized receiver and connection geometry.

Preferably, there are provided a plurality of outer and inner shanks, wherein the inner shanks are designed such that each inner shank may be arranged in the inside of at least one of the outer shanks, and the inner shanks and outer shanks respectively have identically designed receivers. On account of the identically designed receivers, each inner shank and each outer shank may be releasably connected to one and the same working optics or the same optics housing. Preferably, a fitting outer shank is provided for each inner shank. It is thus possible to connect differently dimensioned instrument channels to one and the same working optics or the same optics housing. For example, at the beginning of an examination or operation, first an inner shank with a small cross sectional size may be selected, which makes available an instrument channel with a minimal diameter. If during treatment it is ascertained that a larger instrument channel is required for introducing a larger instrument, the inner shank may be exchanged for an inner shank with a larger cross sectional size. Since an inner shank with a larger cross sectional size usually also has a correspondingly larger outer shank, it is then possible to use a correspondingly larger outer shank, and to connect this to the working optics or the optics housing. Such a set of inner and outer shanks, which preferably are matched to one another in pairs, thus permits an easy adaptability of the endoscope to different application purposes. It is thus not necessary to make available a separate endoscope, with its own working optics, for each required shank cross sectional size.

Preferably, in the set of shanks there is provided at least one pair of inner and outer shanks belonging to one another. In the pair, the outer shank is matched in its dimensions to the associated inner shank.

Usefully, the inner and the outer shank of the pair are identified as belonging together, for example by way of a color marking. This permits associated inner and outer shanks to be easily found amongst a multitude of shank pairs.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 is a longitudinal section of the inner shank of the endoscope according to FIGS. 1 and 2; and FIG. 4A–4E are cross sectional views of the endoscope shank on using inner and outer shanks with different cross sectional sizes.

DETAILED DESCRIPTION OF THE INVENTION

Figure 1:
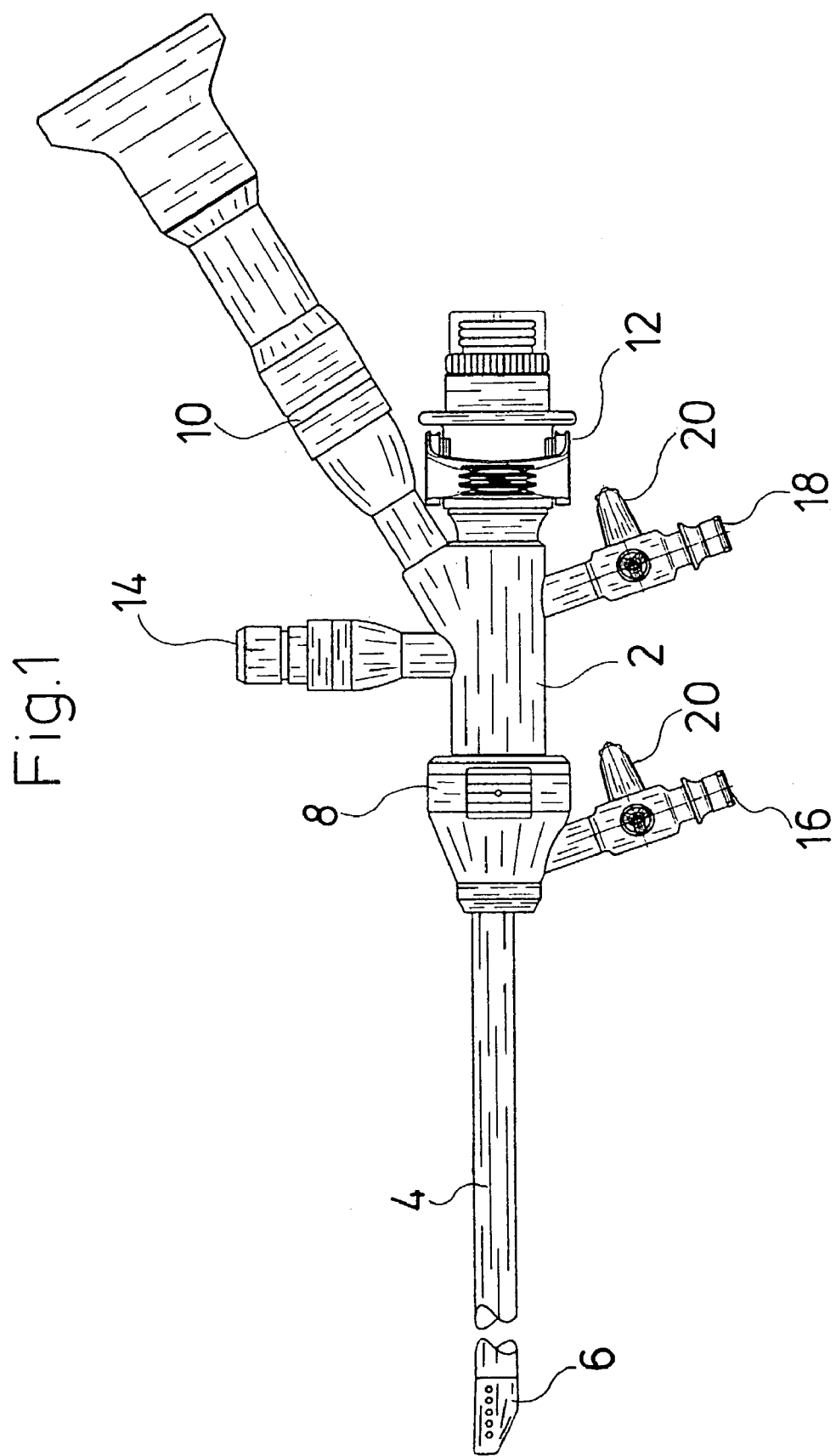
FIG. 1 is an overall side elevation view of an embodiment of an endoscope according to the invention.

The embodiment of the endoscope according to the invention shown in FIG. 1 is a hysteroscope. The endoscope or hysteroscope comprises an optics housing 2 and an attached endoscope shank or outer shank 4. The outer shank 4 at its distal end 6, i.e., at its end distant from the optics housing 2, is open. In the tubular outer shank 4 there are arranged the required endoscope shanks or channels, such as the instrument channel, rinsing channel and optics shank. These shanks or channels may exit the open distal end 6 or are likewise open toward the distal end. At the proximal end 8 of the outer shank 4 there is formed a coupling via which the outer shank 4 is releasably connected to the optics housing 2 in a known manner. The eyepiece 10 of the working optics is bent at an angle to the longitudinal axis of the optics shank of the working optics, i.e., to the longitudinal axis of the outer shank 4, so that in the longitudinal direction of the endoscope or the outer shank 4 an inner shank 12 may be applied at the proximal end of the optics housing 2. The inner shank 12 is preferably open toward the rear or proximal end of the optics housing 2, so that instruments may be introduced into the endoscope through the instrument channel which is formed by the inner shank 12. Furthermore, a fiber-optic cable connection piece 14 is provided in the optics housing. In a known manner, an illumination source is connected to this fiber-optic cable connection piece 14. Furthermore, there are provided two tubing connection pieces 16 and 18 at the proximal end 8 of the outer shank 4 and on the optics housing 2, respectively. The tubing connection pieces 16 and 18 comprise blocking cocks 20 and are connected to rinsing channels in the inside of the endoscope. The rinsing channels are, for example, connected to a suction/rinsing pump for supply and removal of a rinsing fluid via the tubing connection pieces 16 and 18.

Figure 2:
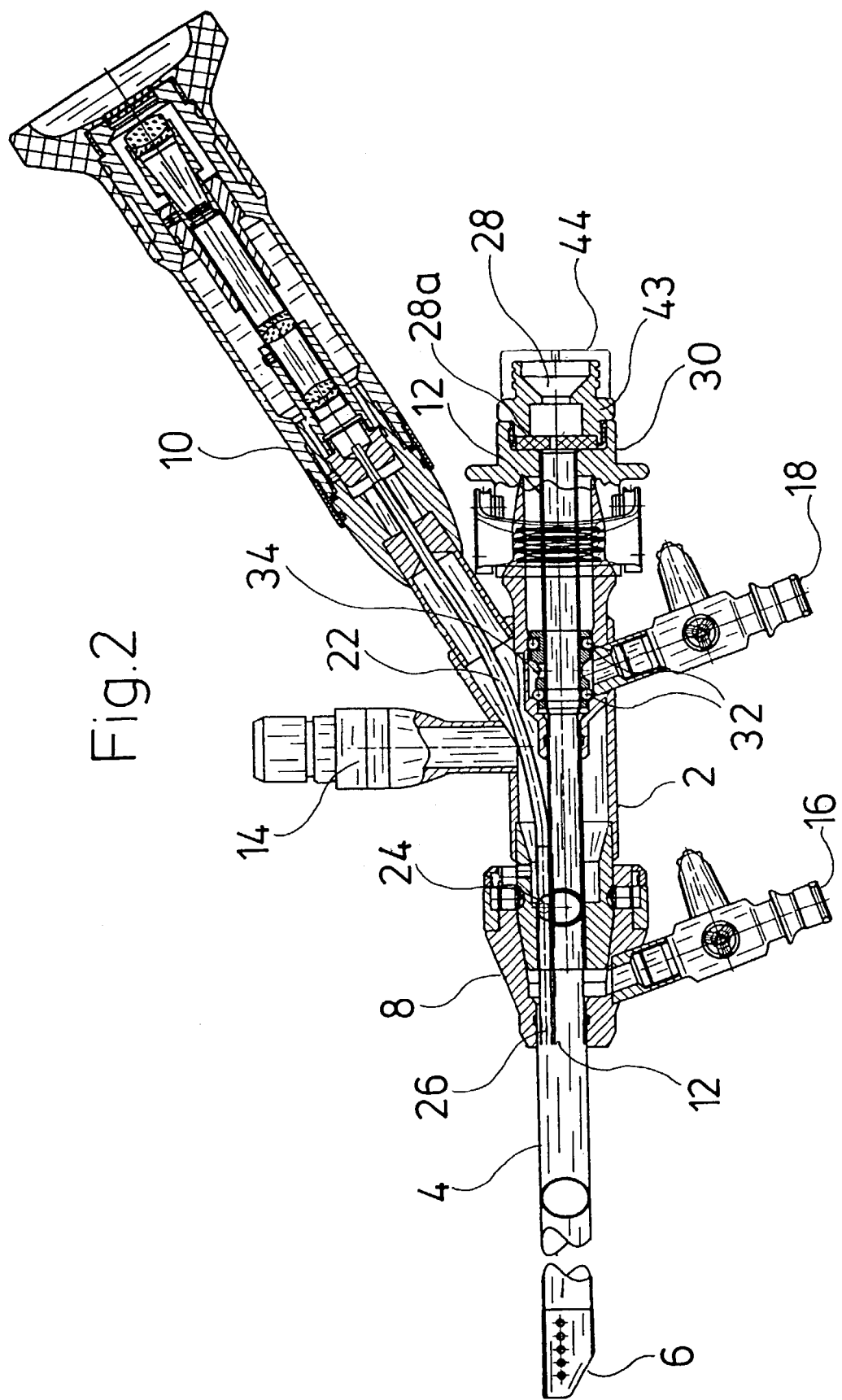
FIG. 2 is a longitudinal section of the endoscope shown in FIG. 1.

FIG. 2 shows a sectional view of the endoscope shown in FIG. 1. The endoscope optics 10, bent at an angle, and the fiber-optic cable connection piece 14 are designed in a known manner, which is why they are not described in more detail. The eyepiece 10 is connected to an image bundle or an individual light fiber-optic or image fiber 22 for image transmission. The proximal-side ends of the fiber-optic fibers or the proximal-side end of the fiber-optic element are fixed in the fiber-optic cable connection piece 14. The image bundle or the individual image fibers 22 as well as the fiber-optic fibers or fiber-optic elements 24 for illuminating are commonly fixed in the distally extending optics shank 26, which extends in the longitudinal direction of and parallel to the outer shank 4. The optics shank 26 has an essentially semicircular cross section, while the image bundle 22 has an essentially circular cross section for image transmission. The image bundle 22 is arranged essentially centrally in the optics shank 26, while the fiber-optic fibers 24 for illumination are arranged circumferentially or laterally to the image bundle 22 in the optics shank 26. The radius of the essentially semicircular optics shank 26 is smaller than the radius of the outer shank 4 which essentially has a circular cross section. The optics shank 26 is arranged eccentrically in the outer shank 4 in its upper region, and may bear on the inner circumference of the outer shank 4.

The outer shank 4 at its proximal end comprises a quick-tension closure 8. The quick-tension closure 8, in a known manner, is designed as a conical tension closure. In the inside of the quick-tension closure 8 there is formed a conical inner circumferential surface which is sealingly placed on a corresponding conical circumferential surface on the optics housing 2. Spring-biased balls serve for locking the two cone elements to one another. Furthermore, the tubing connection piece 16 is attached on the quick-tension closure 8. The tubing connection piece 16 is connected to the inner space of the outer shank 4. The inner space of the outer shank 4 which surrounds the applied instrument shank 12 and the optics shank 26 is used as a first rinsing channel.

An inner shank 12 is applied into the inside of the optics housing 2 as well as into the inside of outer shank 4. The inner shank 12 is essentially tubular in form and has an essentially semicircular cross section. The central longitudinal axis of the inner shank 12 is arranged laterally displaced from the longitudinal axis of the outer shank 4, so that the inner shank 12 as well as the optics shank 26 may be arranged next to one another or over one another in the inside of the outer shank 4. At the same time, the planar surfaces of the semicircular optics shank 26 and of the semicircular inner shank 12 may face one another.

The inner shank 12 is introduced from and into the proximal, i.e. rear end, of the optics housing 2 and the outer shank 4. The inner shank 12 preferably extends over the whole length of the outer shank 4 and opens toward its open end 6. The inner shank 12 defines the instrument channel of the endoscope, through which instruments may be introduced. The inner shank 12 at its proximal or rear end comprises an opening 28, through which the instruments may be introduced into the endoscope or the instrument channel. Likewise, on the rear or proximal end of the inner shank 12 there is arranged a coupling element 30 for the sealed connection of the inner shank 12 to the optics housing 2. The coupling element 30 is likewise designed as a coupling cone connection with a quick-tension closure. In the inside of the coupling element 30 on the inner shank 12 there is formed a conical recess which is sealingly placed onto a cone-shaped or conical surface at the proximal end of the optics housing 2. Furthermore, on the inner shank 12 there are provided two annular seals 32, which seal an annular space 34 with respect to the inside of the optics housing 2. O-rings, for example, may be used as annular seals 32. The annular space 34 is open toward the inside of the inner shank 12. The opening of the tubing connection piece 18 is placed such that the tubing connection piece 18 is open toward the annular space 34. Thus a connection of the tubing connection piece 18 to the inside of the inner shank 2 is created, so that the free lumen in the inside of the inner shank 12 may be used as a second rinsing channel. Since the inner shank 12 is used as a rinsing channel, the opening is sealed toward the outside by way of a sealing element in the form of a sealing cap placed onto the proximal-side end of the inner shank 12, when an instrument is applied into the inner shank 12. If, however, no instrument is located in the inner shank 2, then the sealing is effected via a membrane seal 28a (see also FIG. 3).

The outer shank 4 may be easily separated from the optics housing 2 via the quick-tension closure 8 and replaced with another outer shank 4. For this, the outer shank 4 may be pulled from the optics shank 26 and the inner shank 12. Furthermore, the inner shank 12 via the coupling element 30 may likewise be easily separated from the optics housing 2 and removed to the rear, i.e., in the proximal direction, out of the optics housing 2. It is thus possible to exchange the inner shank 12 and the outer shank 4 for differently dimensioned outer and inner shanks 4, 12. Since the sealing and connection of the outer shank 4 and the inner shank 12 to the optics housing 2 is effected respectively by a standardized quick-tension closure 8 or a standardized coupling element 30, which are formed independently of the diameter of the respective outer and inner shanks, it is possible to sealingly connect differently dimensioned outer and inner shanks to the optics housing 2. The respective connection parts, i.e., coupling element 30 and quick-tension closure 8, for connection to the optics housing 2 are designed equally with all cross sectional sizes of outer and inner shanks.

FIG. 3 shows an individual view of the inner shank 12 used in FIG. 2. Between the annular seals 32 there are arranged radially extending openings 36, which permit access to the inside of the inner shank 12 in order to supply and/or remove rinsing fluid. At the proximal-side or rear end of the inner shank 12 the coupling element 30 is designed for connection to an optics housing 2. The coupling element 30 comprises a coupling cone as well as a closure ring for the locking and sealed connection to the optics housing. Thus, in a known manner, a sealed and easily releasable connection may be created. Furthermore, at the proximal end of the inner shank 12 there may be provided an opening 28, which is sealed by a sealing cap and through which the instruments may be introduced into the instrument channel which is defined by the inner shank 12. Furthermore, in the coupling element 30 there is provided a membrane seal 28a, so that no rinsing fluid may exit from the inner shank 12 at the rear or proximal end. In the embodiment shown the membrane seal 28a, additionally arranged in the coupling element 30, is a fluted sealing disk which, when required, may be easily exchanged, in that the instrument part 43 carrying the sealing cap 44 is screwed out of the coupling element 30.

The FIGS. 4A to 4E show endoscope shanks in cross sectional views, i.e., outer shank 4, inner shank 12, and an optics shank 26 of the endoscope described by way of FIGS. 1 to 3. In each case in the FIGS. 4A to 4E different diameter outer shanks 4 and inner shanks 12 are arranged. The optics shank 26 is always the same, i.e., it has a constant cross sectional size.

FIG. 4A shows an arrangement in which the outer shank 4 is used without an inner shank. The outer shank 4 directly forms an instrument channel into which an instrument 37 is introduced. The cross sectional size or inner diameter of the outer shank 4 is here essentially set by the outer dimensions of the optics shank 26. The optics shank 26 is designed as essentially semicircular. The image bundle or the image transmission element 22 for image transmission is arranged in the central region of the optics shank 26. Arranged laterally to this is the fiber-optic element or the fiber-optic fibers 24 for illumination. The optics shank 26 fills roughly half of the inner cross sectional size of the outer shank 4. The remaining region between the outer shank 4 and the optics shank 26 forms an instrument channel and simultaneously a first rinsing channel 38. The inner cross sectional size or inner diameter of the outer shank is selected such that it just permits the accommodation of the optics shank 26 and the instrument 37. In this manner one creates an endoscope shank or an outer shank 4 with a minimal cross sectional size or outer diameter. With this arrangement only one rinsing channel is available so that an expansion medium is intermittently supplied and led away.

FIG. 4B shows a cross section of the endoscope shank with an outer shank 4 and with an applied inner shank 12. The inner shank 12 is designed essentially semicircular in cross section. In contrast to the outer shank 4 shown in FIG. 4A, the outer shank 4 according to FIG. 4B has a larger cross sectional size, so that it may just accommodate the optics shank 26 and the inner shank 12 in its inside. At the same time, the cross sectional shape of the outer shank 4, which here is essentially circular, is selected in a manner such that a free space 38 remains laterally of the optics shank 26 and the inner shank 12. This free space 38 may, as explained by way of FIG. 4A, be used as a rinsing channel 38. The optics shank 26 is identical to the optics shank 26 according to FIG. 4A, i.e., here it has the same cross section. A working apparatus or instrument 40 may be introduced into the inside of the inner shank 12. Circumferentially of the working apparatus or instrument 40 in the inside of the inner shank 12 there remains a free space 42 which serves as a rinsing channel. For example, the free space 42 may be used for supplying a rinsing fluid, while the free space 38 serves for removal of the rinsing fluid.

FIGS. 4C, 4D and 4E show further arrangements corresponding to the arrangement in FIG. 4B, wherein the outer shanks 4 and the inner shanks 12 in each of the Figures have different cross sectional sizes. The optics shank 26 is, however, identical in all Figures, i.e., it has an identical cross section. The FIGS. 4A to 4E emphasize how differently sized inner shanks 12, i.e., inner shanks with different cross sectional sizes may be applied when using an optics shank 26 which always remains the same. The use of differently sized inner shanks 12 permits the application of instruments with a differently sized cross sectional area. The cross sectional size of the outer shanks 4 is adapted accordingly. At the same time, the cross sectional size or cross sectional shape of the outer shank 4 is selected such that outer dimensions preferably correspond to the minimal diameter with a predetermined cross sectional size of the inner shank 12 and of the optics shank 26. Furthermore, the outer shank 4 and the inner shank 12 may be dimensioned such that the free space 38 between the inner shank 12 and the optic shank 26, on the one hand, and the outer shank 4 has a desired cross sectional size. Thus the cross sectional size of the rinsing channel 38 may be exactly set in order to permit certain through-flow rates. Furthermore, by way of the selection of the cross sectional shape of the inner shank 12, with a pre-determined outer diameter of an instrument, one may influence the size of the free space 42 in the inside of the inner shank 12 in a directed manner, in order to achieve a second rinsing channel with a defined cross sectional size. As has been described by way of FIGS. 1 and 2, all outer shanks 4, which may have different cross sectional sizes and/or shapes, have in common uniform and equally formed and dimensioned couplers or a quick-tension closures 8, with which they may be fastened on an optics housing 2. The different inner shanks 12 mutually and independently of their cross sectional shape and size comprise uniform coupling or connection elements 30 for connection to the optics housing 2. This allows a multitude of different inner shanks 12 and associated outer shanks 4 to be connected to one and the same optics housing 2, so that one may easily provide differently sized working and rinsing channels without having to keep ready a multitude of different endoscopes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An endoscope having a longitudinal direction and proximal and distal ends, the endoscope comprising an optics housing (2) provided at the proximal end, an outer shank (4) releasably connected to the optics housing (2), and an inner shank (12) forming a channel inside the inner shank capable of accommodating introduction of a working instrument, the inner shank (12) running inside and parallel to the outer shank (4) and being releasably connected to the optics housing (2), the inner and outer shanks running in the longitudinal direction, wherein the inner shank (12) is removable from the outer shank (4) without releasing the outer shank (4) from the optics housing (2).

2. The endoscope according to claim 1, wherein an optics shank (26) is arranged inside the outer shank (4) and extends in the longitudinal direction of the outer shank (4).

3. The endoscope according to claim 2, wherein a fiber-optic (24) is arranged in the optics shank (26) for illumination.

4. The endoscope according to claim 2, wherein image transmission optics (22) are arranged in the optics shank (26).

5. The endoscope according to claim 2, wherein the optics shank (26) is releasably connected to the optics housing (2).

6. The endoscope according to claim 1, wherein a free space (38) is formed between the inner shank (12) and an inner wall of the outer shank (4).

7. The endoscope according to claim 2, wherein a free space (38) is formed between the optics shank (26) and an inner wall of the outer shank (4).

8. The endoscope according to claim 1, wherein the outer shank (4) and the inner shank (12) are releasably connected to the optics housing (2) via coupling-cone connections (8, 30).

9. An endoscope set, comprising an optics housing (2), at least one outer shank (4) releasably connectable to the optics housing (2), and at least one inner shank (12) forming a channel inside the inner shank capable of accommodating introduction of a working instrument, the inner shank (12) being arrangeable inside the outer shank (4) and releasably connectable to the optics housing (2), wherein the inner shank (12) is removable from the outer shank (4) without releasing the outer shank (4) from the optics housing (2).

10. The endoscope set according to claim 9, wherein the at least one inner shank (12) is arrangeable inside the outer shank to run eccentrically to the outer shank (4).

11. The endoscope set according to claim 9, comprising a plurality of the inner shanks (12) which are exchangeable.

12. The endoscope set according to claim 11, wherein the plurality of inner shanks (12) have different cross sectional sizes.

13. The endoscope set according to claim 9, comprising a plurality of the outer shanks (4) which are exchangeable.

14. The endoscope set according to claim 13, wherein the plurality of outer shanks (4) have different cross sectional sizes.

15. The endoscope set according to claim 9, further comprising an optics shank (26) arrangeable inside the outer shank (4).

16. The endoscope set according to claim 15, wherein the optics shank (26) is connected to the optics housing (2).

17. The endoscope set according to claim 15, wherein the optics shank (26) is releasably connectable to the optics housing (2).

18. The endoscope set according to claim 15, wherein the optics shank (26) has a cross sectional size which is smaller than an inner cross sectional size of each outer shank (4).

19. A set of shanks for an endoscope, the set comprising a plurality of outer shanks (4) and a plurality of inner shanks (12), wherein the inner shanks (12) are designed such that each inner shank (12) is arrangeable inside at least one of the outer shanks (4), and the inner shanks (12) and the outer shanks (4) have respectively identically designed receivers (8,30) at one end for independent connection to and removal from an optics housing (2) of the endoscope.

20. The set according to claim 19, wherein the plurality of shanks comprises at least one pair of matching inner shank (12) and outer shank (4).

21. The set according to claim 20, wherein the inner shank (12) and the outer shank (4) of the pair are identified as matching.

22. The endoscope according to claim 1, wherein the outer shank (4) and the inner shank (12) are directly connected to the optics housing (2).

23. The endoscope set according to claim 9, wherein the at least one outer shank (4) and the at least one inner shank (12) are directly connectable to the optics housing (2).

24. The set according to claim 19, wherein the identically designed receivers (8, 30) are each directly connectable to the optics housing (2).

* * * * *